United States Patent [19]
Elam

[11] Patent Number: 5,109,838
[45] Date of Patent: May 5, 1992

[54] VISUALLY MONITORED ANESTHESIA BREATHING CIRCUIT

[76] Inventor: James O. Elam, 450 N. 325 East, Valparaiso, Ind. 46383

[21] Appl. No.: 554,381

[22] Filed: Jul. 19, 1990

[51] Int. Cl.$^5$ ............................................. A61M 15/00
[52] U.S. Cl. ........................... 128/203.12; 128/205.12; 128/205.23
[58] Field of Search ...................... 128/202.22, 205.12, 128/205.28, 205.23, 204.18, 203.12, 205.24

[56] References Cited

U.S. PATENT DOCUMENTS

| | | | |
|---|---|---|---|
| 2,837,413 | 6/1958 | Hay | 128/205.28 |
| 2,918,356 | 12/1959 | Hay | 128/205.28 |
| 3,566,867 | 3/1971 | Dryden | 128/205.28 |
| 3,707,965 | 1/1973 | Guzay | 128/205.28 |
| 3,820,959 | 6/1974 | Wise et al. | 128/205.28 |
| 3,830,632 | 8/1974 | Guzay | 128/205.28 |
| 4,051,847 | 10/1977 | Henkin | 128/202.22 |
| 4,108,172 | 8/1978 | Moore, Jr. | 128/205.12 |
| 4,232,667 | 11/1980 | Chalon et al. | 128/205.12 |
| 4,326,514 | 4/1982 | Eian | 128/202.22 |
| 4,488,547 | 12/1984 | Mason | 128/202.22 |

Primary Examiner—Edgar S. Burr
Assistant Examiner—Aaron J. Lewis
Attorney, Agent, or Firm—Wood, Phillips, Mason, Recktenwald & VanSanten

[57] ABSTRACT

In order to visually monitor all aspects of a breathing circuit, a visually monitored anesthesia breathing circuit is disclosed. The circuit includes a transparent absorber having a disposable single use cartridge with particulate carbon dioxide absorbent material therein. The disposable single use cartridge is also formed of a transparent material and is removably positioned within the absorber. The circuit also includes a visual indicator associated with the disposable single use cartridge for indicating the extent of depletion of carbon dioxide absorption potential of the carbon dioxide absorbent material. The absorber includes an expiratory valve in communication with the disposable single use cartridge and an inspiratory valve in communication with the absorber. The circuit further includes fittings for delivering an anesthetic and/or oxygen to a patient in a metered flow. With this arrangement, the circuit also has a humidifier and an overflow valve in communication with the absorber for connection to an operating room scavenger system.

15 Claims, 2 Drawing Sheets

5,109,838

VISUALLY MONITORED ANESTHESIA BREATHING CIRCUIT

FIELD OF THE INVENTION

The present invention relates to an improved device for monitoring gaseous material absorption and, more particularly, to a visually monitored anesthesia breathing circuit.

BACKGROUND OF THE INVENTION

Generally speaking, it is well recognized that a wide variety of devices for the absorption of gaseous material are available. These devices sometimes find applicability in industry where acid or alkaline gases are absorbed in chemical absorption towers, personal rebreathing systems, and the like. For medical applications, it is common practice to utilize a device for absorbing carbon dioxide.

For this application, a patient is typically connected to an anesthesia breathing circuit. This circuit commonly includes a particulate material which has the capacity to absorb the unwanted gaseous material, i.e., carbon dioxide. While anesthesia breathing circuits are now well known, problems remain.

Naturally, one problem involves the capacity of the particulate material to absorb the carbon dioxide. It is generally desirable to be able to determine the rate of absorption of the carbon dioxide by the particulate material but, in particular, it is critical to be aware of the point of exhaustion of the capacity of the material to absorb the unwanted gas. Obviously, in an anesthesia breathing circuit, it is important to replace the particulate material no later in time than the exhaustion point.

In order to achieve this objective, the person monitoring the anesthesia breathing circuit must have an accurate monitoring technique. It is known, of course, that the particulate material commonly utilized includes an indicating means in the form of a chemically absorbed indicating material such as a color indicator which is pH sensitive so as to change color when the absorbent material no longer has the capacity to absorb carbon dioxide. While this represented a significant advance in the field at its introduction, drawbacks still exist.

As will be appreciated by those skilled in the art, the accuracy of the color indicator is suspect. This follows from the fact that there may be an uneven color change throughout the particulate material or even color reversal particularly if operation of the anesthesia breathing circuit is interrupted even for a brief period of time. Because of factors such as these, there has been a need for an improved technique for visually monitoring the absorbent capacity of the material.

In addition to the foregoing, an anesthesia breathing circuit should also have other visual monitoring features. For instance, it is highly desirable to be able to monitor both inspiration and expiration of a patient who is connected to an anesthesia breathing circuit as well as the existence of an overflow condition. As will be appreciated, any such technique must be highly sensitive to the breathing response of the patient.

Of course, the technique should also provide visual monitoring at a mere glance. It is still further recognized that, particularly in connection with overflow, the exact point of overflow should be variable to accommodate the requirements for any particular patient application. As for other requirements, the anesthesia breathing circuit would be more highly effective with a humidification capability.

The present invention is directed to overcoming one or more of the foregoing problems and achieving one or more of the resulting objects by providing an entirely visually monitored anesthesia breathing circuit.

SUMMARY OF THE INVENTION

Accordingly, it is a principal object of the present invention to provide an improved anesthesia breathing circuit. It is a further object of the present invention to provide an anesthesia breathing circuit which is entirely visually monitored. It is still another object of the present invention to visually monitor all aspects of a breathing circuit.

Accordingly, the present invention is directed to a visually monitored anesthesia breathing circuit. The breathing circuit includes an absorber having a pair of spaced apart end walls joined by a generally cylindrically shaped side wall formed of a transparent material. With this arrangement, the breathing circuit includes a disposable single use cartridge having a particulate carbon dioxide absorbent material within the absorber.

As for the disposable single use cartridge, it is defined by a pair of spaced apart, perforated end walls joined by a generally cylindrical side wall. At least the side wall if formed of a transparent material to accommodate visual observation of the particulate carbon dioxide absorbent material through the transparent side wall of the absorber and the transparent side wall of the cartridge. The disposable single use cartridge is removably positioned within the absorber in spaced relation to the side wall and one of the end walls thereof.

Also, the breathing circuit includes means internally adjacent the transparent side wall of the disposable single use cartridge for visually indicating the extent of depletion of carbon dioxide absorption potential of the carbon dioxide absorbent material in the disposable single use cartridge. Specifically, the visual indicating means substantially entirely surrounds the carbon dioxide absorbent material within the disposable single use cartridge and is visibly perceptible externally of the absorber through the transparent side wall thereof.

Further, one of the end walls of the absorber includes an expiratory valve in communication with the disposable single use cartridge. The expiratory valve is adapted to direct expired gas from a patient directly to one of the perforated end walls of the disposable single use cartridge for removal of carbon dioxide. In this connection, carbon dioxide is removed as the expired gas flows through the carbon dioxide absorbent material in the disposable single use cartridge to the other of the perforated end walls.

Still further, one of the end walls of the absorber includes an inspiratory valve in communication with the absorber. The inspiratory valve is adapted to receive anesthetic gases and oxygen for a patient from the other of the perforated end walls of the disposable single use cartridge following removal of carbon dioxide. Specifically, anesthetic gases and oxygen are received after the expired gas flows through the carbon dioxide absorbent material in the disposable single use cartridge and the other of the perforated end walls.

With these features, the breathing circuit also includes external means for delivering an anesthetic to a patient in a metered flow. The external anesthetic delivering means is in communication with the absorber upstream of the inspiratory valve and downstream of the disposable single use cartridge. The inspiratory valve is adapted to provide anesthetic with oxygen from the absorber.

Also, with these features, the breathing circuit includes external means for delivering oxygen to a patient in a metered flow. The external oxygen delivering means is in selectively operable communication with the absorber upstream of the inspiratory valve and downstream of the disposable single use cartridge. The inspiratory valve is adapted to provide a fresh oxygen supply to the patient.

Still additionally, the breathing circuit includes an overflow valve in communication with the absorber. The overflow valve advantageously includes an outlet leading to a scavenger system from a vertically extending valve tube formed on the top wall of the absorber to have a seat for a weighted valve ball radially dimensioned so as to accommodate gas flow through the vertically extending valve tube to the scavenger system when vertically displaced from the valve seat. Advantageously, the valve ball is removable for replacement with a valve ball of a different weight whereby the overflow valve is adjustable to accommodate requirements for any particular patient application.

In a preferred embodiment, the spaced apart end walls of the absorber include a top wall formed to have the expiratory valve and the inspiratory valve formed integrally therewith along with a bottom wall. The expiratory valve then advantageously includes an inlet leading from a patient into a vertically extending valve tube having a valve seat for a valve ball to define a one-way valve. With this arrangement, the expiratory valve also includes a vertically extending flow passage surrounding the valve tube in radially spaced relation along with a dome at the upper end thereof.

Preferably, the dome is disposed in vertically spaced relation to the valve tube to receive the valve ball for permitting expired gas to pass from the valve tube into the flow passage. The flow passage then communicates with an upper one of the perforated end walls of the disposable single use cartridge for passage of expired gas first vertically upward through the valve tube and then vertically downward through the flow passage. With this arrangement, the valve tube and flow passage are transparent to accommodate visual monitoring of expiration by viewing vertical movement of the valve ball between the valve seat and the dome.

Also in the preferred embodiment, the inspiratory valve includes an outlet leading to a patient from a vertically extending valve tube having a valve seat for a valve ball to define a one-way valve. The inspiratory valve also advantageously includes a vertically extending flow passage surrounding the valve tube in radially spaced relation and has a dome at the upper end thereof. The dome is disposed in vertically spaced relation to the valve tube to receive the valve ball to permit inspired gas to pass from the valve tube into the flow passage. With this arrangement, the flow passage communicates with a lower one of the perforated end walls of the disposable single use cartridge for passage of inspired gas first vertically upward through the valve tube and then vertically downward through the flow passage.

As with the expiratory valve, the inspiratory valve is formed such that the valve tube and the flow passage are transparent to accommodate visual monitoring of inspiration by viewing vertical movement of the valve ball between the valve seat and the dome.

As for other aspects of the breathing circuit, the disposable single use cartridge is preferably supported by a perforated vertical support. The perforated vertical support is then disposed between the bottom wall of the absorber and a lower one of the perforated end walls of the disposable single use cartridge. With this structure, the perforated vertical support permits oxygen to flow from the disposable single use cartridge to the inspiratory valve.

In a highly preferred embodiment, the visual indicating means includes a thin substrate treated with a non-fading pH sensitive dye. The dye initially is a first preselected color and changes to a second preselected color after the absorbent material in the disposable single use cartridge has been exposed to carbon dioxide. Advantageously, the thin substrate is paper or fabric and the non-fading pH sensitive dye is an amphoteric aniline dye which is red in color at a pH above approximately 10.0 and yellow in color at a pH below approximately 10.0.

In addition to the foregoing, the carbon dioxide absorbent material is preferably generally white in its unused state. The substrate, which surrounds the absorbent material, advantageously has a stenciled region where the carbon dioxide absorbent material is visible in contrast to the red and/or yellow substrate externally of the absorber. With the contrasting colors of the absorbent material and substrate, it is easy to visually monitor the extent of depletion of the absorbent capacity of the particulate material.

Still other details of the present invention include a flexible elastic breathing bag as the external oxygen delivering means. Alternatively, the external oxygen delivering means may advantageously comprise a mechanical ventilator. In addition, the external anesthetic delivering means may comprise a fitting adapted to connect with a source of anesthetic gases.

One additional important aspect of the present invention includes a water jacket surrounding the absorber. This water jacket is transparent and substantially entirely enclosed and is provided with means for heating the water in order to provide humidification to the patient. Because of the transparent nature of the water jacket, it is still possible to visually monitor the indicating means.

Other objects, advantages and features of the present invention will become apparent from a consideration of the following specification taken in conjunction with the accompanying drawings.

DETAILED DESCRIPTION OF THE PREFERRED EMBODIMENT

Figure 1:
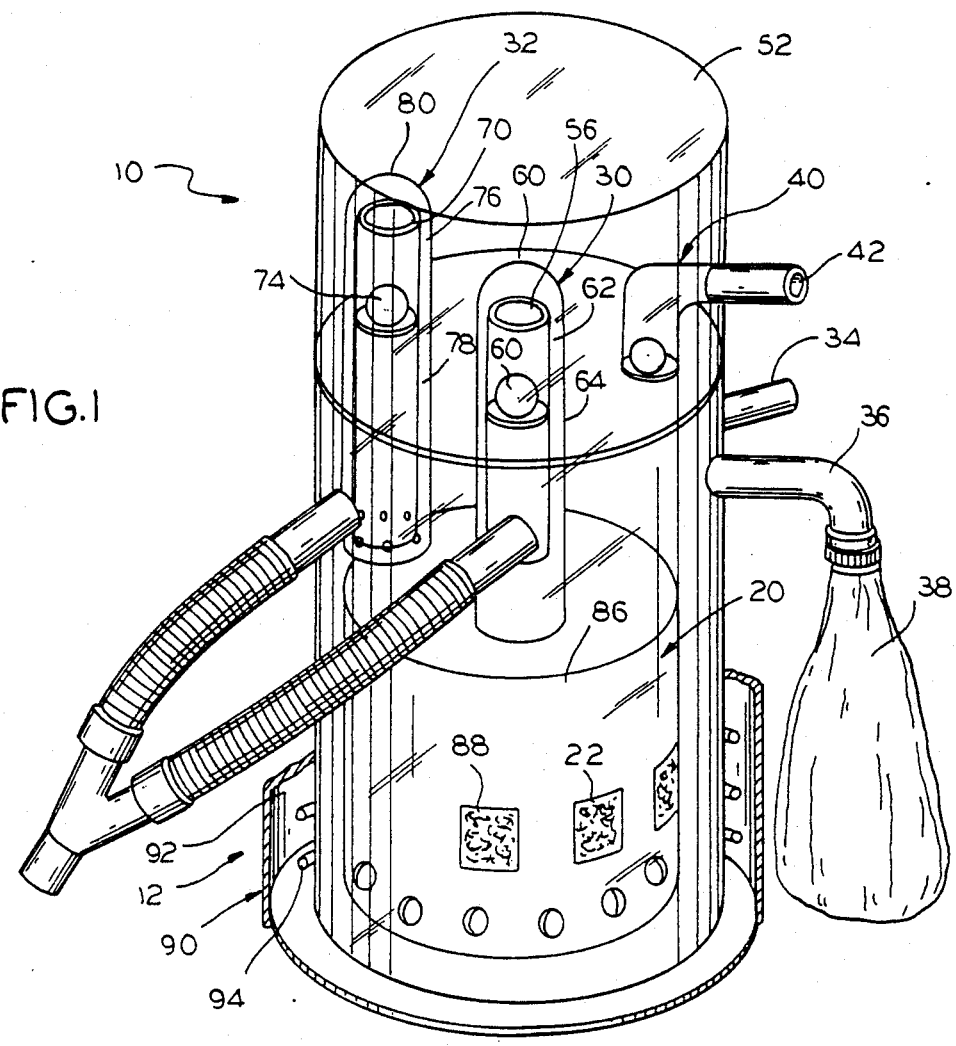
FIG. 1 is a perspective view of a visually monitored anesthesia breathing circuit in accordance with the present invention.

Referring to the drawings, and first to FIG. 1, the reference numeral 10 designates generally a visually monitored anesthesia breathing circuit in accordance with the present invention. The anesthesia breathing circuit 10 includes an absorber generally designated 12 which has a pair of spaced apart end walls 14 and 16 (see FIG. 3) joined by a generally cylindrically shaped side wall 18 formed of a transparent material. As will be appreciated from a consideration of FIG. 3, the anesthesia breathing circuit 10 also includes a disposable single use cartridge generally designated 20 which has a particulate carbon dioxide absorbent material 22 therein.

Figure 3:
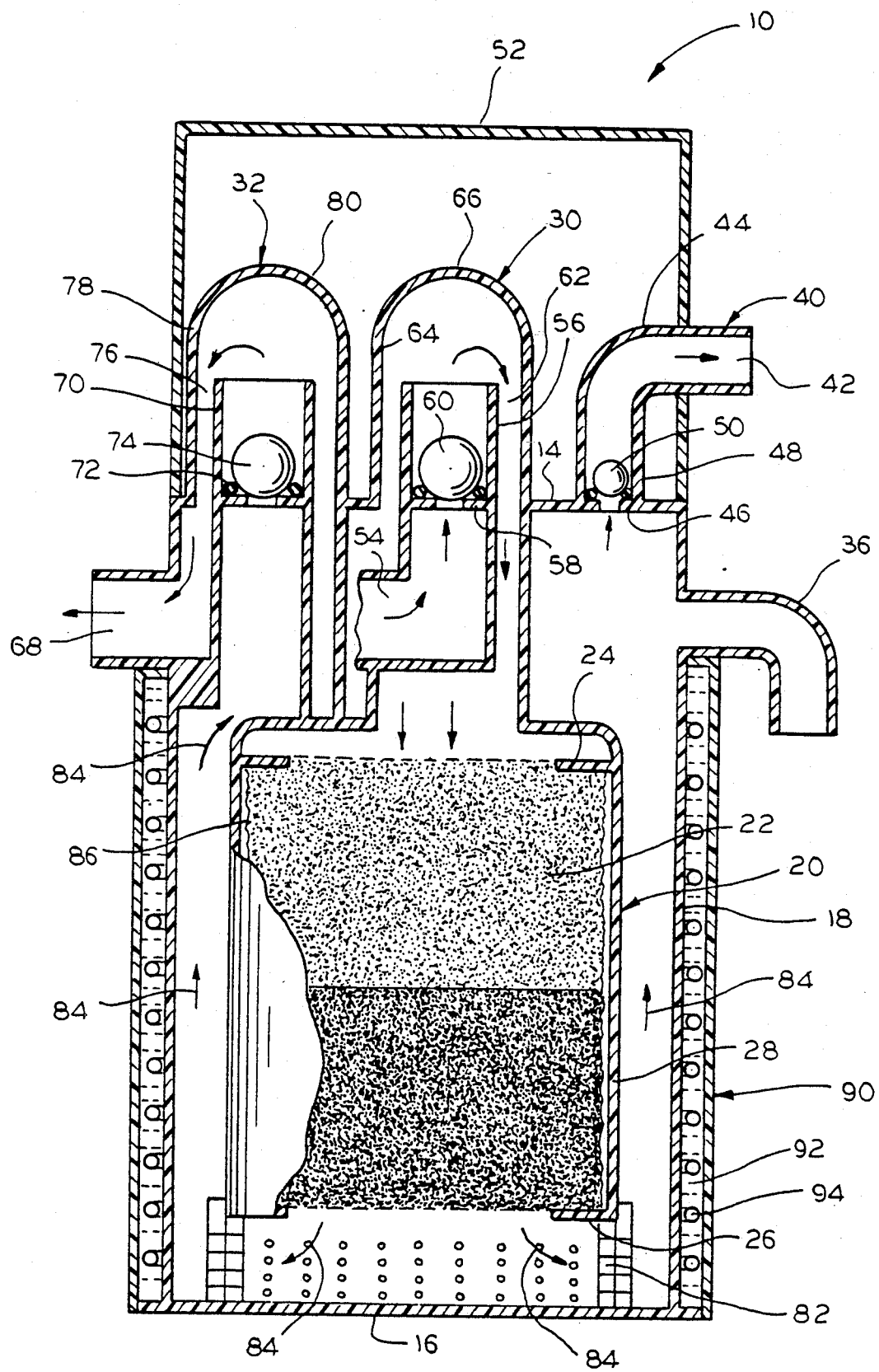
FIG. 3 is a cross-sectional view of the visually monitored anesthesia breathing circuit illustrated in FIG. 1.

Still referring to FIG. 3, the disposable single use cartridge 20 is defined by a pair of spaced apart, perforated end walls 24 and 26 joined by a generally cylindrical side wall 28. At least the side wall 28 is formed of a transparent material. With this arrangement, the disposable single use cartridge 20 is removably positioned within the absorber 12 in spaced relation to the side wall 18 and at least on of the end walls 16 thereof.

As will be appreciated from FIG. 3, the anesthesia breathing circuit 10 also includes means internally adjacent the transparent side wall 28 of the disposable single use cartridge 20 for visually indicating the extent of depletion of carbon dioxide absorption potential of the carbon dioxide absorbent material 22 in the disposable single use cartridge 20. As will be described in detail hereinafter, the visual indicating means substantially entirely surrounds the carbon dioxide absorbent material 22 within the disposable single use cartridge 20 and is visibly perceptible externally of the absorber 12 through the transparent side wall 18 thereof.

Figure 2:
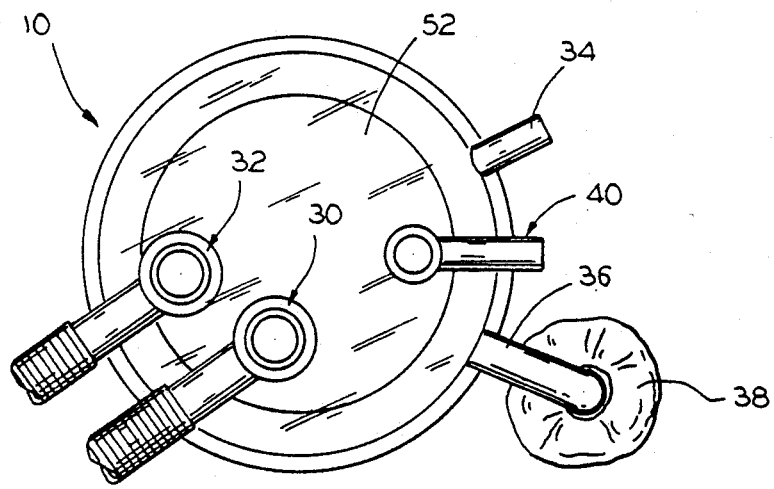
FIG. 2 is a top plan view of the visually monitored anesthesia breathing circuit illustrated in FIG. 1.

As shown in all of FIGS. 1-3, one of the end walls 14 of the absorber 12 includes an expiratory valve 30 in communication with the disposable single use cartridge 20. The expiratory valve 30 is adapted to direct expired gas from a patient directly to one of the perforated end walls 24 of the disposable single use cartridge 20 for removal of carbon dioxide. In this connection, carbon dioxide is removed as the expired gas flows through the carbon dioxide absorbent material 22 in the disposable single use cartridge 20 to the other of the perforated end walls 26.

As will also be seen from FIGS. 1-3, one of the end walls 14 of the absorber 12 includes an inspiratory valve 32 in communication with the absorber 12. The inspiratory valve 32 is adapted to receive oxygen for a patient from the other of the perforated end walls 26 of the disposable single use cartridge 20 following removal of carbon dioxide. In this connection, the oxygen is supplied after the expired gas flows through the carbon dioxide absorbent material 22 in the disposable single use cartridge 20 and the other of the perforated end walls 26.

Referring to FIG. 1, the anesthesia breathing circuit 10 includes external means for delivering an anesthetic to a patient in a metered flow. This may suitably comprise a tubular fitting 34 which is in communication with the absorber 12 upstream of the inspiratory valve 32 and downstream of the disposable single use cartridge 20. As a result, the inspiratory valve 32 is well adapted for providing a patient with anesthetic together with oxygen from the absorber 12.

Also as shown in FIG. 1, the anesthesia breathing circuit 10 includes external means for delivering oxygen to a patient in a metered flow. This, too, may comprise a tubular fitting 36 which may normally carry a squeeze bag 38 to assist the patient with inspiration but which bag 38 may be removed for the purpose of securing the tubular fitting 36 directly to a source of oxygen, i.e., the tubular fitting 36 is in selectively operable communication with the absorber 12 upstream of the inspiratory valve 32 and downstream of the disposable single use cartridge 20. With this understanding, the inspiratory valve 32 is adapted to provide a patient with fresh oxygen supply from the absorber 12.

Referring specifically to FIGS. 1 and 3, the anesthesia breathing circuit 10 further includes an overflow valve 40 in communication with the absorber 12 for connection to an operating room scavenger system. The overflow valve 40 includes an outlet 42 leading to the scavenger system from a vertically and then horizontally extending valve tube 44 formed on the top wall 14 of the absorber 12 to have a seat 46 defined in part by an O-ring 48 for a weighted valve ball 50 which is radially dimensioned so as to accommodate gas flow through the vertically and then horizontally extending valve tube 44 to the scavenger system (not shown) when the ball 50 is vertically displaced from the valve seat 48. In accordance with the invention, the valve ball 50 is removable through the oversized valve tube 44 for replacement with a valve ball of a different weight.

By reason of this fact, the overflow valve 40 is adjustable. It will be appreciated that, by selecting from a plurality of valve balls such as 50 having different weights, the overflow valve adjustability feature can be accomplished in a unique fashion. As a result, the overflow valve 44 is adapted to accommodate the requirements for any particular patient application.

Referring specifically to FIG. 3, it will be seen that the spaced apart end walls 14 and 16 of the absorber 12 include a top wall 14 and a bottom wall 16. It will also be appreciated that the top wall 14 is formed so as to have the expiratory valve 30 and the inspiratory valve 32 formed integrally therewith. In this manner, the absorber 12 comprises a sealed chamber isolated from the top portion 52 of the anesthesia breathing circuit 10 (see FIG. 1).

Referring once again to FIG. 3, the expiratory valve 30 includes an inlet 54 leading from a patient into a vertically extending valve tube 56 having a valve seat 58 for a valve ball 60 to define a one-way valve. The expiratory valve 30 also includes a vertically extending flow passage 62 surrounding the valve tube 56 in radially spaced relation wherein the flow passage 62 is defined by a tube 64 having a dome 66 at the upper end thereof. The dome 66 is disposed in vertically spaced relation to the valve tube 56 to receive the valve ball 60 to permit expired gas to pass from the valve tube 56 into the flow passage 62. The flow passage 62 communicates with an upper one of the perforated end walls 24 of the disposable single use cartridge 20 for passage of expired gas first vertically upward through the valve tube 56 and then vertically downward through the flow passage 62. With this arrangement, the valve tube 56, flow passage 62, surrounding tube 64, and dome 66 are transparent to accommodate visual monitoring of expiration by viewing vertical movement of the valve ball 60 between the valve seat 58 and the dome 66.

Still referring to FIG. 3, the inspiratory valve 32 includes an outlet 68 leading to a patient from a vertically extending valve tube 70 having a valve seat 72 for a valve ball 74 to define a one-way valve. The inspiratory valve 32 also includes a vertically extending flow passage 76 surrounding the valve tube 70 in radially spaced relation wherein the flow passage 76 is defined by a tube 78 having a dome 80 at the upper end thereof. The dome 80 is disposed in vertically spaced relation to the valve tube 70 to receive the valve ball 74 so as to permit inspired gas to pass from the valve tube 70 into the flow passage 76. The flow passage 76 communicates with a lower one of the perforated end walls 26 of the disposable single use cartridge 20 for passage of inspired gas first vertically upward through the valve tube 70 and then vertically downward through the flow passage 76. With this arrangement, the valve tube 70, the flow passage 76, the surrounding tube 78, and the dome 80 are transparent to accommodate visual monitoring of inspiration by viewing vertical movement of the valve ball 74 between the valve seat 72 and the dome 80.

Referring to FIG. 3, the anesthesia breathing circuit 10 also includes a perforated vertical support 82 for the disposable single use cartridge 20 The perforated vertical support 82 is integral with the bottom wall 16 of the absorber 12 and disposed between the bottom wall 16 and a lower one of the perforated end walls 26 of the disposable single use cartridge 20. With this arrangement, the perforated vertical support 82 permits oxygen to flow from the disposable single use cartridge 20 to the inspiratory valve 32 as shown by the arrows 84.

Still referring to FIG. 3, the visual indicating means includes a thin substrate 86 treated with a non-fading pH sensitive dye. The dye initially is a first preselected color and changes to a second preselected color after the absorbent material 22 in the disposable single use cartridge 20 has been exposed to carbon dioxide sufficiently to deplete its carbon dioxide absorbent potential. Preferably, the thin substrate 86 is either paper or fabric and the non-fading pH sensitive dye is an amphoteric aniline dye.

In a preferred embodiment, the amphoteric aniline dye is red in color at a pH above approximately 10.0 and yellow in color at a pH below approximately 10.0. Also, the carbon dioxide absorbent material is preferably generally white in color when it still has its full carbon dioxide absorbent potential such that the substrate 86 can advantageously have a stenciled region as at 88 where the carbon dioxide absorbent material 22 is clearly visible in contrast to the red and/or yellow substrate 86 externally of the absorber 12. Still further, the carbon dioxide absorbent material 22 is preferably changes color from white to purple after depletion of its carbon dioxide absorption potential As previously mentioned, the tubular fitting 36 can serve two purposes. It can, as shown in FIG. 1, have a flexible elastic breathing bag 38 attached thereto for aiding in the inspiration of oxygen which is provided from expiration of carbon dioxide that has passed through the disposable single use cartridge 20. Alternatively, the tubular fitting 36 may be connected to a conventional mechanical ventilator (not shown).

Again referring to FIG. 3, the anesthesia breathing circuit 10 advantageously includes a water jacket 90 surrounding the absorber 12. This water jacket is a sealed chamber 92 containing water as well as heating means such as a heating coil 94 whereby the absorber 12 can be warmed so as to provide humidified oxygen from the moisture created from the expired air that is converted into oxygen. In other words, the water jacket 90 warms the gas mixture inspired by the patient.

While in the foregoing there has been set forth a preferred embodiment of the invention, it will be appreciated that the details herein given may be varied by those skilled in the art without departing from the true spirit and scope of the appended claims.

I claim:

1. A visually monitored anesthesia breathing circuit, comprising:

an absorber having a pair of spaced apart end walls joined by a side wall, said spaced apart end walls of said absorber including a top wall and a bottom wall and said side wall being formed of a transparent material and being generally cylindrically shaped, and a disposable single use cartridge having a particulate carbon dioxide absorbent material therein;

said disposable single use cartridge being defined by a pair of spaced apart, perforated end walls joined by a generally cylindrical side wall, at least said side wall being formed of a transparent material, said disposable single use cartridge being removably positioned within said absorber in spaced relation to said side wall and one of said end walls thereof;

means internally adjacent said transparent side wall of said disposable single use cartridge for visually indicating the extent of depletion of carbon dioxide absorption potential of said carbon dioxide absorbent material in said disposable single use cartridge, said visual indicating means substantially entirely surrounding said carbon dioxide absorbent material within said disposable single use cartridge and being visibly perceptible externally of said absorber through said transparent side wall thereof;

one of said end walls of said absorber including an expiratory valve in communication with said disposable single use cartridge and including an inspiratory valve in communication with said absorber;

said expiratory valve being adapted to direct expired gas from a patient directly to one of said perforated end walls of said disposable single use cartridge for removal of carbon dioxide as said expired gas flows through said carbon dioxide absorbent material in said disposable single use cartridge to the other of said perforated end walls;

said expiratory valve including an inlet leading from a patient into a vertically extending valve tube, said valve tube having a valve seat for a valve ball to define a one-way expiration monitoring valve, said expiratory valve also including a vertically extending flow passage surrounding said valve tube in radially spaced relation, said flow passage having a dome at the upper end thereof, said dome being disposed in vertically spaced relation to said valve tube to receive said valve ball to permit expired gas to pass from said valve tube onto said flow passage, said flow passage communicating with an upper one of said perforated end walls of said disposable single use cartridges for passage of expired gas first vertically upward through said valve tube and then vertically downward through said flow passage, said expiratory valve including said valve tube and said flow passage being transparent to accommodate visual monitoring of expiration by viewing vertical movement of said valve ball between said valve seat and said dome;

said inspiratory valve being adapted to receive anesthetic gases and oxygen for a patient from the other of said perforated end walls of said disposable single use cartridge following removal of carbon dioxide after said expired gas flows through said carbon dioxide absorbent material in said disposable single use cartridge and the other of said perforated end walls;

said inspiratory valve including an outlet leading to a patient from a vertically extending valve tube, said valve tube having a valve seat for a valve ball to define a one-way inspiration monitoring valve, said inspiratory valve also including a vertically extending flow passage surrounding said valve tube in radially spaced relation, said flow passage having a dome at the upper end thereof, said dome being disposed in vertically spaced relation to said valve tube to receive said valve ball to permit inspired gas to pass from said valve tube into said flow passage, said flow passage communicating with a lower one of said perforated end walls of said disposable single use cartridge for passage of inspired gas first vertically upward through said valve tube and then vertically downward through said flow passage, said inspiratory valve including said valve tube and said flow passage being transparent to accommodate visual monitoring of inspiration by viewing vertical movement of said valve ball between said valve seat and said dome;

external means for delivering an anesthetic to a patient in a metered flow, said external anesthetic delivering means being in communication with said absorber upstream of said inspiratory valve and downstream of said disposable single use cartridge, said inspiratory valve being adapted to provide anesthetic with oxygen from said absorber;

external means for delivering oxygen to a patient in a metered flow, said external oxygen delivering means being in selectively operable communication with said absorber upstream of said inspiratory valve and downstream of said disposable single use cartridge, said inspiratory valve being adapted to provide a fresh oxygen supply from said absorber; and an overflow valve in communication with said absorber for connection to an operating room scavenger system.

2. The visually monitored anesthesia breathing circuit of claim 1 wherein said top wall is formed to have said expiratory valve and said inspiratory valve formed integrally therewith.

3. A visually monitored anesthesia breathing circuit, comprising:

an absorber having a pair of spaced apart end walls joined by a side wall, said spaced apart end walls of said absorber including a top wall and a bottom wall and said side wall being formed of a transparent material and being generally cylindrically shaped, and a disposable single use cartridge having a particulate carbon dioxide absorbent material therein;

said disposable single use cartridge being defined by a pair of spaced apart, perforated end walls joined by a generally cylindrical side wall, at least said side wall being formed of a transparent material, said disposable single use cartridge being removably positioned within said absorber in spaced relation to said side wall and one of said end walls thereof;

means internally adjacent said transparent side wall of said disposable single use cartridge for visually indicating the extent of depletion of carbon dioxide absorption potential of said carbon dioxide absorbent material in said disposable single use cartridge, said visual indicating means substantially entirely surrounding said carbon dioxide absorbent material within said disposable single use cartridge and being visibly perceptible externally of said absorber through said transparent side wall thereof;

one of said end walls of said absorber including an expiratory valve in communication with said disposable single use cartridge and including an inspiratory valve in communication with said absorber;

said expiratory valve being adapted to direct expired gas from a patient directly to one of said perforated end walls of said disposable single use cartridge for removal of carbon dioxide as said expired gas flows through said carbon dioxide absorbent material in said disposable single use cartridge to the other of said perforated end walls;

said inspiratory valve being adapted to receive anesthetic gases and oxygen for a patient from the other of said perforated end walls of said disposable single use cartridge following removal of carbon dioxide after said expired gas flows through said carbon dioxide absorbent material in said disposable single use cartridge and the other of said perforated end walls;

external means for delivering an anesthetic to a patient in a metered flow, said external anesthetic delivering means being in communication with said absorber upstream of said inspiratory valve and downstream of said disposable single use cartridge, said inspiratory valve being adapted to provide anesthetic with oxygen from said absorber;

external means for delivering oxygen to a patient in a metered flow, said external oxygen delivering means being in selectively operable communication with said absorber upstream of said inspiratory valve and downstream of said disposable single use cartridge, said inspiratory valve being adapted to provide a fresh oxygen supply from said absorber; and an overflow valve in communication with said absorber for connection to an operating room scavenger system, said overflow valve including an outlet leading to a scavenger system from a vertically extending valve tube, said valve tube being formed on said top wall of said absorber to have a seat for a weighted valve ball, said valve ball being radially dimensioned so as to accommodate gas flow through said vertically extending valve tube to said scavenger system when vertically displaced from said valve seat.

4. The visually monitored anesthesia breathing circuit of claim 3 wherein said valve ball is removable for replacement with a valve ball of a different weight, said overflow valve being adjustable by selecting from a plurality of valve balls of different weights to accommodate requirements for any particular patient application.

5. The visually monitored anesthesia breathing circuit of claim 1 including a perforated vertical support for said disposable single use cartridge, said perforated vertical support being disposed between said bottom wall of said absorber and a lower one of said perforated end walls of said disposable single use cartridge, said perforated vertical support permitting oxygen to flow from said disposable single use cartridge to said inspiratory valve.

6. A visually monitored anesthesia breathing circuit, comprising:

an absorber having a pair of spaced apart end walls joined by a side wall, said side wall being formed of a transparent material and being generally cylindrically shaped, and a disposable single use cartridge having a particulate carbon dioxide absorbent material therein;

said disposable single use cartridge being defined by a pair of spaced apart, perforated end walls joined by a generally cylindrical side wall, at least said side wall being formed of a transparent material, said disposable single use cartridge being removably positioned within said absorber in spaced relation to said side wall and one of said end walls thereof;

means internally adjacent said transparent side wall of said disposable single use cartridge for visually indicating the extent of depletion of carbon dioxide absorption potential of said carbon dioxide absorbent material in said disposable single use cartridge, said visual indicating means substantially entirely surrounding said carbon dioxide absorbent material within said disposable single use cartridge and being visibly perceptible externally of said absorber through said transparent side wall thereof, said visual indicating means including a thin substrate treated with a non-fading pH sensitive dye, said dye initially being a first preselected color and changing to a second preselected color after said absorbent material in said disposable single use cartridge has been exposed to carbon dioxide;

one of said end walls of said absorber including an expiratory valve in communication with said disposable single use cartridge and including an inspiratory valve in communication with said absorber;

said expiratory valve being adapted to direct expired gas from a patient directly to one of said perforated end walls of said disposable single use cartridge for removal of carbon dioxide as said expired gas flows through said carbon dioxide absorbent material in said disposable single use cartridge to the other of said perforated end walls;

said inspiratory valve being adapted to receive anesthetic gases and oxygen for a patient from the other of said perforated end walls of said disposable single use cartridge following removal of carbon dioxide after said expired gas flows through said carbon dioxide absorbent material in said disposable single use cartridge and the other of said perforated end walls;

external means for delivering an anesthetic to a patient in a metered flow, said external anesthetic delivering means being in communication with said absorber upstream of said inspiratory valve and downstream of said disposable single use cartridge, said inspiratory valve being adapted to provide anesthetic with oxygen from said absorber;

external means for delivering oxygen to a patient in a metered flow, said external oxygen delivering means being in selectively operable communication with said absorber upstream of said inspiratory valve and downstream of said disposable single use cartridge, said inspiratory valve being adapted to provide a fresh oxygen supply from said absorber and an overflow valve in communication with said absorber for connection to an operating room scavenger system.

7. The visually monitored anesthesia breathing circuit of claim 6 wherein said thin substrate is paper.

8. The visually monitored anesthesia breathing circuit of claim 6 wherein said thin substrate is fabric.

9. The visually monitored anesthesia breathing circuit of claim 6 wherein said non-fading pH sensitive dye is an amphoteric aniline dye.

10. The visually monitored anesthesia breathing circuit of claim 9 wherein said amphoteric aniline dye is red at a pH above approximately 10.0 and yellow at a pH below approximately 10.0.

11. The visually monitored anesthesia breathing circuit of claim 10 wherein said carbon dioxide absorbent material is generally white and said substrate has a stenciled region where said carbon dioxide absorbent material is visible in contrast to said red and/or yellow substrate externally of said absorber.

12. The visually monitored anesthesia breathing circuit of claim 1 wherein said external oxygen delivering means comprises a flexible elastic breathing bag.

13. The visually monitored anesthesia breathing circuit of claim 1 wherein said external oxygen delivering means comprises a mechanical ventilator.

14. The visually monitored anesthesia breathing circuit of claim 1 wherein said absorber has a gas pathway vertically downward from said expiratory valve through said disposable cartridge and then vertically upward to said inspiratory valve between said absorber and said disposable cartridge.

15. A visually monitored anesthesia breathing circuit, comprising:

an absorber having a pair of spaced apart end walls joined by a side wall, said side wall being formed of a transparent material and being generally cylindrically shaped, and a disposable single use cartridge having a particulate carbon dioxide absorbent material therein;

said disposable single use cartridge being defined by a pair of spaced apart, perforated end walls joined by a generally cylindrical side wall, at least said side wall being formed of a transparent material, said disposable single use cartridge being removably positioned within said absorber in spaced relation to said side wall and one of said end walls thereof;

means internally adjacent said transparent side wall of said disposable single use cartridge for visually indicating the extent of depletion of carbon dioxide absorption potential of said carbon dioxide absorbent material in said disposable single use cartridge, said visual indicating means substantially entirely surrounding said carbon dioxide absorbent material within said disposable single use cartridge and being visibly perceptible externally of said absorber through said transparent side wall thereof;

one of said end walls of said absorber including an expiratory valve in communication with said disposable single use cartridge and including an inspiratory valve in communication with said absorber;

said expiratory valve being adapted to direct expired gas from a patient directly to one of said perforated end walls of said disposable single use cartridge for removal of carbon dioxide as said expired gas flows through said carbon dioxide absorbent material in said disposable single use cartridge to the other of said perforated end walls;

said inspiratory valve being adapted to receive anesthetic gases and oxygen for a patient from the other of said perforated end walls of said disposable single use cartridge following removal of carbon dioxide after said expired gas flows through said carbon dioxide absorbent material in said disposable single use cartridge and the other of said perforated end walls;

external means for delivering an anesthetic to a patient in a metered flow, said external anesthetic delivering means being in communication with said absorber upstream of said inspiratory valve and downstream of said disposable single use cartridge, said inspiratory valve being adapted to provide anesthetic with oxygen from said absorber;

external means for delivering oxygen to a patient in a metered flow, said external oxygen delivering means being in selectively operable communication with said absorber upstream of said inspiratory valve and downstream of said disposable single use cartridge, said inspiratory valve being adapted to provide a fresh oxygen supply from said absorber;

an overflow valve in communication with said absorber for connection to an operating room scavenger system; and a water jacket surrounding at least said side wall of said absorber, said water jacket comprising a sealed chamber having means for heating water therewithin, said heated water being adapted to warm said absorber to thereby warm gases inspired by a patient.

* * * * *